United States Patent [19]

Langer

[11] 4,164,946

[45] Aug. 21, 1979

[54] FAULT DETECTION CIRCUIT FOR PERMANENTLY IMPLANTED CARDIOVERTER

[75] Inventor: Alois A. Langer, Pittsburgh, Pa.

[73] Assignee: Mieczyslaw Mirowski, Owing Mills, Md.

[21] Appl. No.: 801,300

[22] Filed: May 27, 1977

[51] Int. Cl.$^2$ ............................................. A61N 1/36
[52] U.S. Cl. ............................................. 128/419 D
[58] Field of Search ............ 128/419 D, 2.06 A, 2.1 P

[56] References Cited

U.S. PATENT DOCUMENTS

| | | | |
|---|---|---|---|
| 3,138,151 | 6/1964 | Chapman et al. | 128/2.06 A |
| 3,612,041 | 10/1971 | Ragsdale | 128/2.06 A |
| 3,703,900 | 11/1972 | Holznagel | 128/419 D |
| 3,886,932 | 6/1975 | Suessmilch | 128/2.1 P |
| 3,952,750 | 4/1976 | Mirowski et al. | 128/419 D |

OTHER PUBLICATIONS

Stratbucker et al., "Rocky Mountain Engineering Society", 1965, pp. 57-61.
Schuder et al., "Transactions of the American Society for Artificial Internal Organs", vol. XVI, 1970, pp. 207-212.

Primary Examiner—William E. Kamm
Attorney, Agent, or Firm—Fleit & Jacobson

[57] ABSTRACT

Disclosed is a permanently implantable cardioverter, or defibrillator including built-in interrogation and testing circuitry. Implanted fault detection circuits react to malfunctions in the implanted fibrillation detection circuitry, and ensure that inappropriate defibrillation pulses are not delivered to the wearer. Also disclosed is an implantable externally actuatable interrogation and test circuit which interrogates the sensing circuitry for faults, and which delivers a realistic defibrillation pulse to an implanted test load. An external device for monitoring the operation of the implanted defibrillator is also disclosed.

13 Claims, 3 Drawing Figures

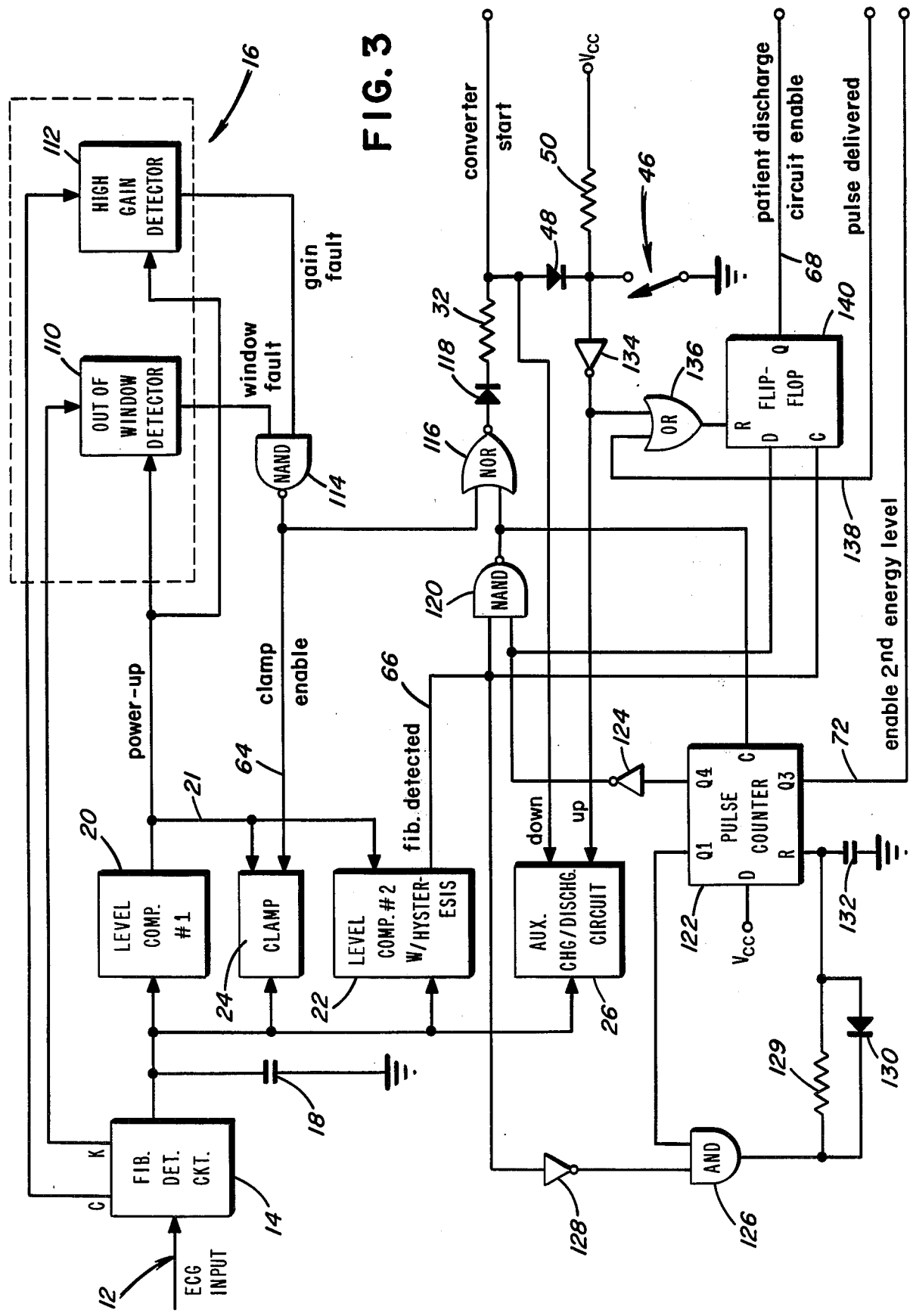

FAULT DETECTION CIRCUIT FOR PERMANENTLY IMPLANTED CARDIOVERTER

BACKGROUND OF THE INVENTION

In recent years, great strides have been made in the development of the implantable defibrillator. See, for example, U.S. Pat. Nos. Re. 27,652 and Re. 27,757, for disclosures of the first fully implantable standby ventricular defibrillator. This art has steadily been developing, and it is expected that within the near future, it will be common for high risk patients to be wearing implanted standby ventricular defibrillators.

Because the implanted ventricular defibrillator could stand as the last link between the sustenance of life and death by reason of ventricular fibrillation, it is important that techniques be developed for ensuring the proper functioning of the implanted circuitry. One approach has already been developed, and is disclosed in U.S. Pat. No. 3,952,750. This patent discloses an externally actuatable implantable circuit which is capable of delivering defibrillating pulses to an implanted test load to verify the operation of the charging and discharge circuits.

Notwithstanding the significant advances which have taken place since the development of the first fully implantable standby ventricular defibrillator, there is much room in the art for advancement. For at the present time, while it is possible to evaluate the condition of the charging and discharge circuits, the operation of the fibrillation detection circuitry cannot be verified.

It is toward filling the aforementioned void in the art, that the present invention is directed.

SUMMARY OF THE INVENTION

The present invention relates to the field of cardioversion, and specifically to interrogation circuitry which is permanently implantable as a part of a cardioverter such as a complete ventricular defibrillator system. More particularly, the inventive interrogation circuitry is designed to continually monitor the operation of the implanted fibrillation detection circuitry, and to disable the discharge section of the defibrillator in the event that a malfunction is detected. The inventive circuitry is capable of deactuating the discharge circuit for a brief period of time if the sensed malfunction is temporary, or permanently deactuating the discharge circuit if the sensed malfunction is permanent.

"Cardioverting" or "cardioversion" as used herein is intended to encompass the correction of a number of arrhythmic heart conditions, both lethal and non-lethal. Those arrhythmic heart conditions include atrial tachycardia, atrial flutter, atrial fibrillation, junctional rhythms, ventricular tachycardia, ventricular flutter, and ventricular fibrillation, and any other non-pacemaking related arrhythmic condition which may be corrected by applying electrical shocks to the heart. Obviously then, "defibrillation" is included in the term cardioversion as a method of applying electrical shocks to the heart to defibrillate fibrillating atria or fibrillating ventricles.

The inventive interrogation circuitry may be actuated from external to the wearer, whereby a specially designed digital readout system provides information indicative of the operation of the fibrillation detector circuitry, the condition of the battery, and the condition of the high-energy capacitor and the discharge circuit. The inventive interrogation circuitry also has a two-stage "power up" operation so that battery life is prolonged. Furthermore, the circuit has many safeguards for either deactuating the discharge circuit or ensuring that discharge is through an implanted test load in the presence of circuit malfunction.

It is accordingly a principal object of the present invention to provide a fully implantable defibrillator having built-in circuitry for interrogating the fibrillation detection circuitry.

A more specific object of the present invention is to provide implantable circuits for detecting faults in the fibrillation detection circuitry, and for blocking the delivery of defibrillation pulses in the event that a fault is detected.

Another object of the present invention is to provide implantable circuitry which can be externally actuated to interrogate an implanted fibrillation detection circuit.

Yet another object of the present invention is to provide implantable circuitry which can be externally actuated to interrogate an implanted fibrillation detection circuit, and to initiate the delivery of a defibrillating pulse to an implanted test load.

A further object of the present invention is to provide a fully implantable interrogation circuit having a two-stage "power up" capability in order to prolong battery life.

Still a further object of the present invention is to provide an external apparatus for associating with a fully implanted defibrillator, for interrogating the implanted defibrillator, and for monitoring the operation of the implanted circuitry and the condition of certain of its components.

These and other objects of the present invention, as well as many of the attendant advantages thereof, will become more readily apparent when reference is made to the following description, taken in conjunction with the accompanying drawings.

BRIEF DESCRIPTION OF THE DRAWINGS

FIG. 3 is a generalized block diagram similar to that shown in FIG. 1, but illustrating the logic circuitry in greater detail.

DETAILED DESCRIPTION OF THE DRAWINGS

Figure 1:
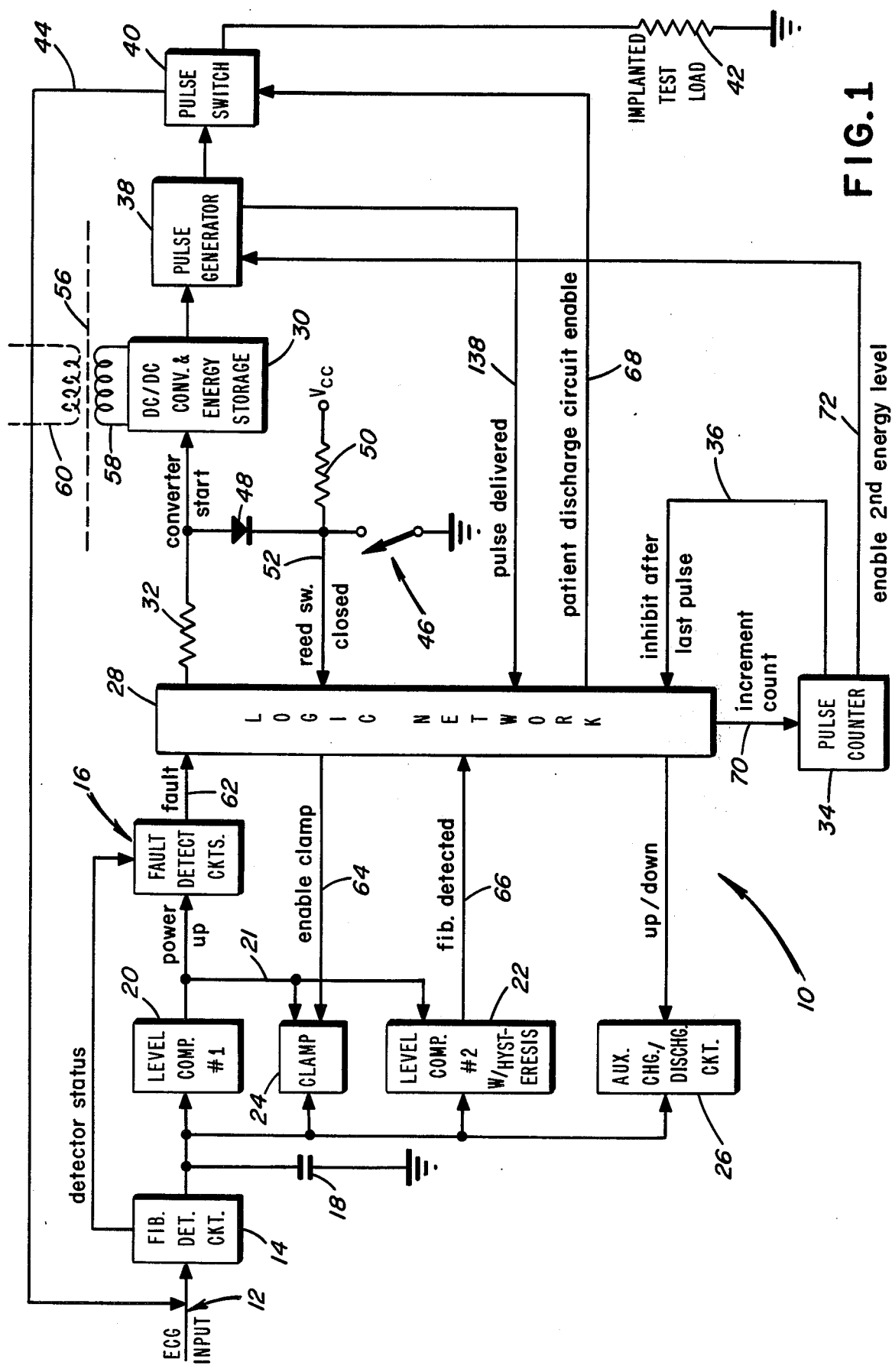
FIG. 1 is a generalized block diagram of a fully implantable defibrillator constructed in accordance with the teachings of the present invention.

With reference first to FIG. 1, the generalized block diagram of the inventive implantable defibrillator will be described. The defibrillator is shown generally at 10, and includes implanted sensing and defibrillating electrodes which are shown generally at 12. The electrodes 12 serve as sensing elements, and ECG input signals are fed to a fibrillation detection circuit 14 by means of electrodes 12.

Fibrillation detection circuit 14 associates with several components independent circuits and circuit elements. The status of the fibrillation detection circuit 14 is monitored by fault detect circuits shown generally at 16. At the same time, the output of the fibrillation detection circuit 14 is simultaneously fed to a fibrillation capacitor 18, a first level comparator 20, a second level comparator 22, a clamp 24 and an auxiliary charge/discharge circuit 26.

A logic network 28 communicates with the fault detector circuits 16, the second level comparator 22, the clamp 24 and the auxiliary charge/discharge circuit 26. In addition, logic network 28 associates with a DC/DC convertor and energy storage circuit 30, through a resistor 32, and with a pulse counter 34. In series with the converter and energy storage circuit 30 is a pulse generator 38 and a pulse switch 40. Pulse switch 40, in turn, associates both with an implanted test load 42 and the electrodes 12 through leads 44. As illustrated at 36, pulse counter 34 feeds back into logic network 28.

A reed switch 46 is connected between resistor 32 and the DC/DC convertor 30 through a diode 48. The junction between reed switch 46 and diode 48 receives biasing potential through a resistor 50, and is connected to the logic network 28 through a line 52. The implanted reed switch 46 is adapted to associate with an external magnet. See FIG. 2, wherein such a magnet is shown at 54. There, the skin of the wearer is represented by dash line 56. Also adapted to be coupled across skin line 56 is an implanted coil 58 of DC/DC converter 30, and an external coil 60.

The operation of the circuit illustrated in FIG. 1 is as follows. The ECG input is taken from leads 12, and fed to fibrillation detection circuit 14. Assuming the presence of fibrillation, and that circuit 14 is fully operational, fibrillation detection circuit 14 will issue an output current, and fibrillation capacitor 18 will begin to charge. Once capacitor 18 charges to a predetermined low-level threshold, 1.2 volts, for example, the first level comparator 20 is enabled. Then, by way of line 21, other circuits are "powered up" from their normally quiescent states. In order to conserve battery power, the power level in these circuits is increased only upon the input to the first level comparator 20 reaching the low-level threshold.

The next step in the logical sequence is for fault detection circuits 16 to interrogate select functions of the fibrillation detection circuit 14. In the event that a fault is detected, circuits 16 issue a fault signal on line 62, which signal is fed to logic network 28, resulting in the issuance of a signal on line 64 to enable clamp 24. At this occurrence, clamp 24 holds the fibrillation capacitor 18 to a value below the threshold of the second level comparator 22. In the event that the fault in the fibrillation detection circuit 14 is permanent, the condition described above is maintained. On the other hand, if the fault is only temporary, then the fault signal on line 62 will be removed.

Assuming that the fibrillation circuit 14 is operating without fault, and that fibrillation is present, capacitor 18 will continue to charge until it reaches the threshold level of comparator 22. Comparator 22 is then enabled, and a "fibrillation detected" signal is fed to logic network 28 by means of line 66. Logic network 28 then initiates the delivery of a defibrillation pulse.

While not a necessity, the inventive circuit is designed such that once a "fibrillation detected" signal is received by logic network 28, a "down" command is issued to auxiliary charge/discharge circuit 26. As a result, fibrillation capacitor 18 is discharged, and this discharge continues until such time as the voltage on capacitor 18 falls below the threshold value of the second level comparator 22. During the discharge of the fibrillation capacitor, a pulse is being issued on the "converter start" line, and the DC/DC converter 30 is enabled.

Actuation of the DC/DC converter 30 initiates the charging of an internal energy storage capacitor (not shown), the status of which is monitored by pulse generator 38. Once the energy storage capacitor is charged to a predetermined level, the charge is released by pulse generator 38 and, assuming that pulse switch 40 is set to deliver an actual defibrillating pulse, the capacitor is discharged into the heart of the wearer by means of line 44 leading to electrodes 12.

It will be noted that the state of pulse switch 40 is controlled by logic network 28 through line 68. The preceding paragraph described the situation where pulse switch 40 is in its state suitable to deliver an actual defibrillating pulse. In its other state, pulse switch 40 associates the energy storage capacitor with the implanted test load 42. As a result, rather than discharging the energy storage capacitor into the heart of the wearer, the capacitor is discharged into the implanted test load 42.

Upon the delivery of a defibrillating pulse into the heart, an "increment count" signal is issued by the logic network 28 on line 70; this signal is received by pulse counter 34. If defibrillation is successful, defibrillation circuit 10 returns to its standby state. On the other hand, if fibrillation is still present, a command signal is issued on line 72, and pulse generator 38 is instructed to discharge the energy storage capacitor only when charged to a second, and higher energy level. Then, once such higher energy level is achieved, pulse generator 38 again releases the energy storage capacitor for discharge into the heart. A further increment count is issued on line 70, and is counted by pulse counter 34. Then, after the delivery of some predetermined number of attempted defibrillating pulses, four for example, it can be assumed that the wearer cannot be saved. Accordingly, after the last of such attempts, an inhibit signal is issued on line 36, and the defibrillation circuit 10 is shut down.

The foregoing description was based upon fully automatic operation of the defibrillation circuit 10. With the inventive circuit, however, it is possible to initiate the interrogation and test firing functions at will. In this regard, the magnet 54 (FIG. 2) is positioned against the skin 56 of the wearer adjacent the position of reed switch 46. As a result, reed switch 46 closes, and pulse switch 40 is switched so as to discharge the energy storage capacitor into the implanted test load 42.

Upon actuation of reed switch 46, the logic network 28 issues an "up" signal to the auxiliary charge/discharge circuit 26, and initiates the charging of defibrillator capacitor 18. Capacitor 18 begins to charge, and results in the operation of fault detector circuits 16 once the threshold level of comparator 20 is reached. Then, if no faults are detected, capacitor 18 continues to charge until it reaches the threshold level of comparator 22. A "fibrillation detected" signal is then issued on line 66, and the discharge of the energy storage capacitor continues as described above, with discharge being through the implanted test load 42.

Figure 2:
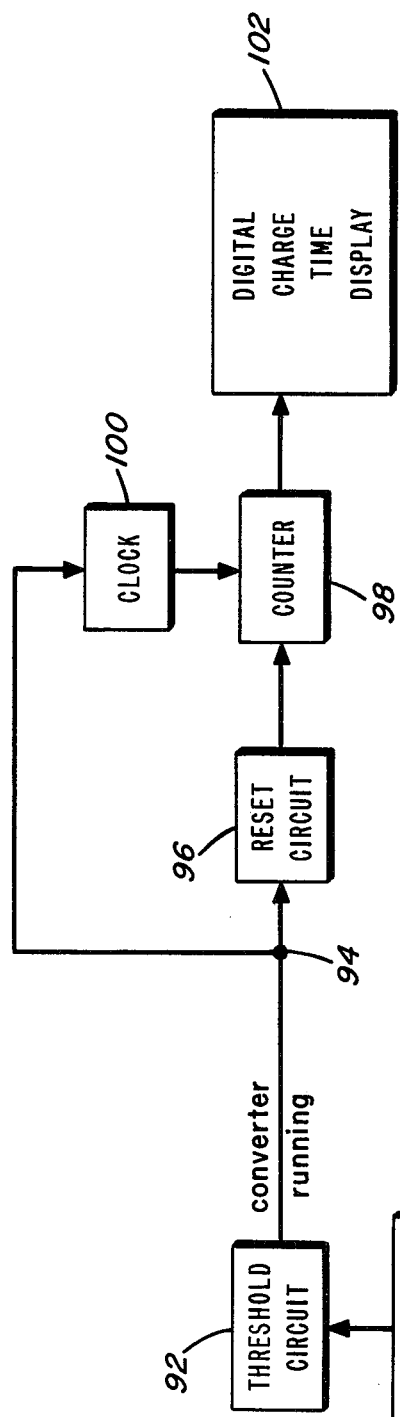
FIG. 2 is a generalized block diagram of an external device for monitoring the operation of the defibrillator illustrated in FIG. 1.
Figure 2:
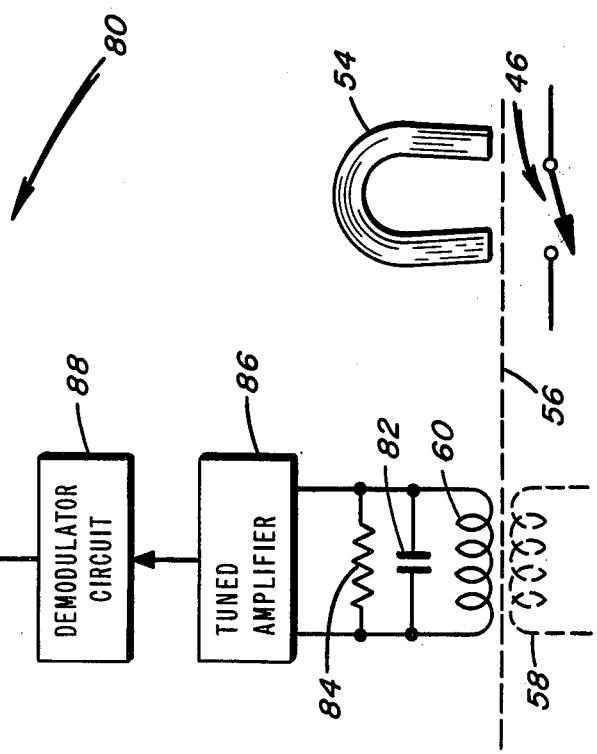

With reference now to FIG. 2, the external monitoring device will be described. This device is shown generally at 80 and includes, as noted above, a coil 60 which couples to the implanted coil 58 of the DC/DC convertor 30. Coil 60, capacitor 82 and resistor 84 define a tuned circuit, tuned to the frequency of implanted coil 58.

In operation, when the DC/DC converter 30 is operative, coil 58 becomes active and, in the presence of pickup coil 60, a high frequency signal will be delivered to a tuned amplifier 86. After amplification, the high frequency signal delivered across the skin 56 of the wearer is demodulated (converted to DC) by means of a demodulator circuit 88, and is then amplified by a DC amplifier 90.

A threshold circuit 92 serves to provide a sharp transition which indicates whether the DC/DC converter 30 is operative or is idle. Assuming that the converter 30 is operating, threshold circuit 92 will issue a "converter running" signal on line 94, will actuate a reset circuit 96, and will cause a counter 98 to reset. A clock 100 pulses the counter 98, and the output of counter 98 is digitally displayed on a digital charge time display unit 102.

When the DC/DC converter 30 ceases its operation, the output of the threshold circuit 92 will be discontinued, and the last output of counter 98 will remain on the display of digital charge time display 102. Then, should converter 30 again become operative, the "converter running" signal issued by threshold circuit 92 will reset counter 98 through the means of reset circuit 96, and the digital charge time display circuit 102 will also be reset.

The digital readout of display circuit 102 contains much information about the functioning of the implanted defibrillator circuit 10. For example, if reed switch 46 is triggered by magnet 54 and threshold circuit 92 fails to operate (resulting in no readout on display 102), a fault in the fibrillation detector circuit 14 is indicated. On the other hand, proper operation is indicated if the display shows a charge time within defined limits. Yet progressively increasing charge times would indicate battery depletion. Accordingly, by periodically instituting interrogation of the implanted defibrillation circuit 10 by means of external device 80, maximum protection of the wearer can be ensured.

Reference should now be made to FIG. 3, which is quite like the block diagram illustrated in FIG. 1. In this regard, it should be noted that the elements which are the same, are similarly numbered, and that the differences only will be described.

In FIG. 3, the fault detection circuits 16 are shown to include an out of window detector 110 and a high gain detector 112, the respective outputs of which are fed to a NAND gate 114. The output of NAND gate 114, in turn, forms one input to a NOR gate 116 which, through a diode 118, associates with the previously-described resistor 32 and defines the "converter start" line. The remaining input to NOR gate 116 originates from a NAND gate 120, the output of which NAND gate is simultaneously fed to the clock input of a pulse counter 122. As can be seen, one of the inputs to NAND gate 120 is the "fibrillation detected" signal on line 66 from the second level comparator 22. The other input to NAND gate 120 is from the Q4 output of pulse counter 122, through an inverter 124.

An AND gate 126 is also the recipient of the "fibrillation detected" signal from level comparator 22, after the signal is inverted by an inverter 128. The other input to AND gate 126 is from the Q1 output of pulse counter 122. The output of AND gate 126 feeds through the parallel connection of a resistor 129 and a diode 130, and to a capacitor 132 connected to the reset input of pulse counter 122. The Q3 output of pulse counter 122, as can be seen, forms the second energy enable line 72.

The auxiliary charge/discharge circuit 26 illustrated in FIG. 3 has separate "up" and "down" inputs. The "down" input originates from the junction between resistor 32 and diode 48. The "up" input, on the other hand, originates at the output of an inverter 134. The output of inverter 134 also serves as one input to an OR gate 136, the other input of which is the "pulse delivered" line designated 138.

The output of OR gate 136 serves as the reset input of a D-type flip-flop 140. That is, a signal on the "D" of flip-flop 140 is transmitted through the flip-flop to the "Q" output when the "C" input is clocked. Here, the "D" input of flip-flop 140 takes the form of the inverted Q4 signal from pulse counter 122. The clock input to flip-flop 140 is the "fibrillation detected" signal on line 166. The Q output of flip-flop 140, as can be seen, controls the operation of pulse switch 40 (FIG. 1) through the patient discharge circuit enable line 68.

The operation of the circuit illustrated in FIG. 3 is as follows. When fibrillation is detected by the fibrillation detector circuit 14, the fibrillation capacitor 18 begins to charge toward Vcc. At some predetermined low threshold level, on the order of 1.2 volts, for example, level comparator 20 switches, the "power up" line goes high, and through line 21, the second level comparator 22, the clamp 24, the out of window detector 110 and the high gain detector 112 are actuated. In this way, battery power is conserved.

It should be appreciated that the defibrillation detection circuit can take many forms, and can hence be interrogated in several ways. Here, for purposes of illustration, it is assumed that the fibrillation detector circuit is of the type described in U.S. Patent Application Ser. No. 620,025, filed on Sept. 30, 1975.

While the entire fibrillation detector circuit will not be described, suffice it to say that the detector circuit includes automatic gain control capabilities, and detects fibrillation by evaluating the period of time that a filtered ECG signal spends outside a predetermined window. Accordingly, the fault detect circuits 16 include an out of window detector 110 and a high gain detector 112.

After the first level comparator 20 actuates the two fault detect circuits, the interrogation of the fibrillation detector circuit 14 begins. First, the out of window detector 110 looks to see whether the filtered ECG signal is out of the detector's window for more than a predetermined length of time. For if the filtered ECG signal stays out of the window for more than one to two seconds, a malfunction is indicated.

In the event that such a malfunction is detected, a low "window fault" signal is issued by the out of window detector 110, and is fed to NAND gate 114. A "clamp enable" signal is then issued on line 64, and the clamp 24 is actuated so that the fibrillation capacitor 18 is held at below the threshold of the second level comparator 22.

In the event that detector 110 senses no fault, its output remains high, and the next interrogation of the fibrillation detection circuit 14 commences. Specifically, the high gain detector 112 interrogates the fibrillation detector circuit 14 to determine if the gain is higher than a predetermined threshold. If the gain is in fact higher, as could be caused by, for example, a faulty AGC capacitor, then the high gain detector 112 issues a low "gain fault" output signal, and transmits the same to NAND gate 114. The low "gain fault" signal from detector 112 actuates NAND gate 114 and initiates the same operational sequence as did the low "window fault" signal issued by detector 110. Accordingly, a fault condition start is inhibited since a low on either of the two fault detect lines causes the output of NAND gate 114 to go high, thereby forcing a low condition at the output of NOR gate 116, the main pulse generator enable line.

With the fibrillation detection circuit 14 fully operational, and with fibrillation present, capacitor 18 continues to charge until it eventually reaches the threshold of the second level comparator 22. At this occurrence, a high "fibrillation detected" signal is issued on line 66. This results in flip-flop circuit 140 being clocked, and the patient discharge circuit being enabled. In this regard, assuming that pulse counter 122 has been cleared and that outputs Q1, Q3 and Q4 are low, the output of NAND gate 120 goes low. Since there are no faults, both inputs of NOR gate 116 are low, the output of NOR gate 116 is high, and the "converter start" line initiates operation of the DC/DC converter and energy storage circuit 30 (FIG. 1.).

Notwithstanding that converter circuit 30 has been actuated, further charging of the energy storage capacitor could be interrupted by closing reed switch 46. In this regard, switch 46 is positioned near the output of the circuitry to give maximum override capability over any other fault conditions which would conceivably occur in the logic. In the event that reed switch 46 is closed, the "converter start" line is pulled low through diode 48, and the operation of the DC/DC converter is interrupted. It should also be noted that the value of resistor 50 is quite large, so that should diode 48 become shorted, there would not be enough current to start the converter 30. Also, it should be noted that closing of reed switch 46 resets flip-flop 140, and at worst condition, the test load 42 (FIG. 1) would be pulsed.

With neither a fault being detected nor reed switch 46 being actuated, normal operation of the circuit would continue. A high level signal on the converter start line initiates the discharge of fibrillation capacitor 18 by issuing a "down" signal to the auxiliary charge/discharge circuit 26. It should be noted that circuit 26 is normally in its floating output state when both the "up" and "down" lines are low. Fibrillation capacitor 18 continues to discharge until it decays to the low threshold limit of the second level comparator 22, and the "fibrillation detected" signal on line 66 is removed. As a result, the output of NAND gate 120 goes high, clocking pulse counter 122, and the output Q1 of pulse counter 122 goes high. At the same time, a high level signal into NOR gate 116 causes the "converter start" line to go low, providing a pulse on the "converter start" line.

The DC/DC converter 30 is designed so that it is self-sustaining after oscillations begin. Accordingly, a single pulse on the "converter start" line is sufficient to sustain operation of converter 30. Then, pulses from the converter 30 continue to appear on the "down" line of the charge/discharge circuit 26, holding fibrillation capacitor 18 low, and ensuring a proper capacitor state after a defibrillating pulse is delivered. Upon delivery of such a pulse, flip-flop 140 is reset, through OR gate 136, after a "pulse delivered" signal appears on line 138.

The system is actively held off until a pulse is delivered and the converter 30 stops running. If the pulse is successful, the system will shut down, reverting to its low current state, and the auxilary charge/discharge circuit 26 is disabled. The output of AND gate 126 is now high, and pulse counter 122 will be reset after about 10 to 20 seconds, marking the end of a fibrillation episode.

If the defibrillating pulse is not successful, on the other hand, the detector will cycle again, repeating the sequence. When the fibrillation detected line 66 again goes high, the output of AND gate 126 goes low, preventing the reset of pulse counter 122; the pulse counter 122 is clocked at the end of the "fibrillation detected" pulse. As the circuit is designed, on the fourth pulse, output Q4 goes high, holding the output of NAND gate 120 high. Accordingly, the converter start line is inhibited when the "fibrillation detected" line goes high for the fifth time. Flip-flop 140 is therefore not reset, maintaining the patient discharge enable line 68 low. Under such conditions, the auxiliary charge/discharge circuit 26 is not enabled, and the "fibrillation detected" line remains high so long as fibrillation is sensed. The output of AND gate 126 is low, and the pulse counter 122 is not reset until about 20 seconds after fibrillation is no longer sensed. No additional pulses are then delivered.

The fault detection circuitry will now further be discussed, but in further detail. Assuming that a fault condition is responsible for the charging of fibrillation capacitor 18, one of the two fault detection circuits 110 or 112 would issue a low output signal. The output of NAND gate 114 would then go high, and the "converter start" line would stay low. A high level output from NAND gate 114 enables clamp 24, and keeps fibrillation capacitor 18 from charging to the level of the second level comparator 22.

Two conditions are now possible—the fault is temporary, or it is permanent. If the fault is permanent, the circuit will remain in its quiescent state, and the faulty implant can be identified on the patient's next examination by the attending physician. If the fault is temporary, its presence will cease to be detected by one of the fault detection circuits 110 or 112, and clamp 24 will be disabled. The function of clamp 24 is to ensure that the level of fibrillation capacitor 18 is significantly below the threshold of level comparator 22, when the fault condition is cleared. This provides a delay allowing the detector to resume proper operation before the threshold level of the second level comparator 22 can be reached. Without the presence of clamp 24, the "converter start" line could go high immediately after the clearing of a fault. It should further be noted that NOR gate 116 and clamp 24 provide redundant inhibition of the "converter start" line in the event that a fault is detected.

It was already described when reference was made to FIG. 1, that the inventive circuit can be interrogated from external to the wearer. This is initiated through reed switch 46, which serves both to allow reliable inhibition of the device in the event that a fault condition exists, and to initiate a test mode sequence. The test mode sequence is as follows.

When reed switch 46 is closed, the output of inverter 134 goes high, resetting flip-flop 140 and causing the auxiliary charge/discharge 26 to begin to charge the fibrillation capacitor 18 by the issuance of an "up" command. It should be apparent that circuit 26 is able to operate independently of a "power up" command from level comparator 20.

Once the charge on fibrillation capacitor 18 exceeds the threshold of level comparator 20, the two fault test circuits are actuated. If no faults are detected, the test mode continues. When the threshold of level comparator 22 is reached, the "converter start" line goes high, but the flip-flop 140 is not set due to the presence of a reset signal from OR gate 136. The output of NOR gate 116 also goes high, but the "converter start" enable line is held low through diode 48, which goes to ground through closed reed switch 46.

When the reed switch 46 is released, a high signal appears on the converter start line, and a "down" signal is fed to charge/discharge circuit 26. Accordingly, the discharge of the fibrillation capacitor throughout the operation of the DC/DC converter 30 is ensured. It should also be noted that the signal on the patient discharge circuit enable line 62 is low, and hence that the test load 42 is pulsed, rather than the implanted electrodes.

Advantageously, the above-described test mode exercises a large portion of the implanted circuitry; the result is a comprehensive test. The fibrillation detection circuit 14 is thoroughly interrogated, much of the logic is operated, the energy storage capacitor is fully charged, and a realistic defibrillation pulse is discharged into the test load. And importantly, the results of the internal interrogation testing can be displayed on an external digital charge time display, and a significant amount of information can be gained about the operation of the implanted device.

Above, a specific embodiment of the present invention has been described. It should be appreciated, however, that this embodiment was described for purposes of illustration only, without any intention of limiting the scope of the present invention. Rather, it is the intention that the present invention be limited not by the above but only as is defined in the appended claims.

What is claimed is:

1. A discrete fully implantable interrogation circuit for use with a fully implantable cardioverter having a discrete fibrillation detector circuit made up of a plurality of components, each of which produces a characteristic output signal when said fibrillation detector circuit is functioning properly, said detector circuit serving to monitor an ECG signal and to issue a fibrillation detected signal when predetermined characteristics of said ECG signal are detected, and further having an energy storage device, means for charging the energy storage device to a level capable of defibrillating a malfunctioning heart, and means for initiating the discharge of the energy storage device into the heart of a wearer, said discrete fully implantable interrogation circuit comprising: fault detector means for monitoring the output signal of a select number of said components to determine whether said output signal is not within prescribed limits so as to cause said fibrillation detector circuit to misinterpret said ECG signal; and disabling means associated with said fault detector means for inhibiting the discharge of said storage device into the heart of the wearer in the event that said fault detector means senses a malfunction in said fibrillation detector circuit by recognizing an output signal not within said prescribed limits.

2. The interrogation circuit recited in claim 1, and further comprising: enable means for powering said fault detector means in the event that said fibrillation detector circuit detects fibrillation.

3. The interrogation circuit recited in claim 1, wherein said fibrillation detector circuit includes means for automatically controlling the gain of an ECG signal, and means for detecting fibrillation by evaluating the period of time that said gain-controlled ECG signal spends outside a predetermined window, and wherein said fault detector means comprises an out of window detector associated with said fibrillation detector circuit for detecting whether said gain-controlled ECG signal is outside said predetermined window for more than a predetermined length of time, and a high gain detector associated with said fibrillation detector circuit for detecting whether the output of said gain-controlling means is higher than a predetermined threshold.

4. The interrogation circuit recited in claim 1, and further comprising: a fully implantable test load; and a fully implantable pulse switch for controlling whether said energy storage device discharges into the heart of the wearer or into said implantable test load.

5. The interrogation circuit recited in claim 4, and further comprising: control means for placing said pulse switch to a state whereby said energy storage means associates with said test load in the event that any circuit malfunction is sensed.

6. The interrogation circuit recited in claim 4, and further comprising: fully implantable switch means for initiating operation of the interrogation circuit upon external actuation.

7. The interrogation circuit recited in claim 6, and further comprising means for external actuation, by temporarily disabling said defibrillator, prior to initiating the operation of the interrogation circuit.

8. The interrogation circuit recited in claim 1, and further comprising: means for determining the state of said disabling means from external to the wearer.

9. The interrogation circuit recited in claim 8, wherein said means for charging the energy storage device includes an implanted coil, and further comprising magnetic coupling means associated with said implanted coil for sensing when the same is active and hence when the energy storage device is being charged.

10. The interrogation circuit recited in claim 1, and further comprising means for determining the state of said disabling means by sensing the operation of said means for charging the energy storage device during the course of an interrogating cycle.

11. The interrogation circuit recited in claim 1, and further comprising: means for initiating a complete test cycle of said defibrillator upon external command.

12. For use with a fully implantable defibrillator having a fibrillation detection circuit, an energy storage device, means for charging the energy storage device to a level sufficient to defibrillate a malfunctioning heart, means for discharging the energy storage device into the heart, interrogation circuitry for interrogating the fibrillation detection circuit to detect any malfunctions therein, a fully implantable test load, and a fully implantable switch for discharging the energy storage device into the heart or into the test load, an external monitoring device comprising: sensing means for sensing the time interval between the initiation of charging the energy storage device and the discharge of the energy storage device into the test load; and display means for displaying said time interval.

13. For use with a fully implantable cardioverter having a discrete fibrillation detector circuit made up of a plurality of components, each of which produces a characteristic output signal when said fibrillation detector circuit is functioning properly, said detector circuit serving to monitor cardiac electrical activity and to issue a first signal in response to the detection of fibrillation, and further having an energy storage device, charging means for charging the energy storage device to a level capable of defibrillating a malfunctioning heart, and discharging means for initiating the discharge of the energy storage device into the heart of a wearer, a discrete fully implantable interrogation circuit comprising: fault detecting means made operable in response to said first signal for monitoring the output signal of a selected number of said components and for issuing a fault signal when at least one of the selected output signals is not within prescribed limits so as to cause said fibrillation detector circuit to misinterpret said cardiac electrical activity; fibrillation signal means responsive to said first signal for issuing a fibrillation detected signal; means responsive to said fibrillation detected signal for first actuating said charging means and then actuating said discharging means; and disabling means responsive to said fault signal for disabling said fibrillation signal means to prevent the discharge of said energy storage device into the heart of the wearer.

* * * * *